(12) United States Patent
Hatlestad et al.

(10) Patent No.: US 7,343,199 B2
(45) Date of Patent: Mar. 11, 2008

(54) MEASUREMENT OF RESPIRATORY SINUS ARRHYTHMIA USING RESPIRATORY AND ELECTROGRAM SENSORS IN AN IMPLANTABLE DEVICE

(75) Inventors: John Hatlestad, Maplewood, MN (US); Qingsheng Zhu, Wexford, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 645 days.

(21) Appl. No.: 10/330,693

(22) Filed: Dec. 27, 2002

(65) Prior Publication Data
US 2004/0127804 A1   Jul. 1, 2004

(51) Int. Cl.
*A61B 5/04* (2006.01)

(52) U.S. Cl. ...................... 600/513; 600/508

(58) Field of Classification Search ............... 600/513, 600/484, 529, 20; 607/20
See application file for complete search history.

(56) References Cited

U.S. PATENT DOCUMENTS

| | | | |
|---|---|---|---|
| 4,519,395 A | | 5/1985 | Hrushesky |
| 4,576,179 A | * | 3/1986 | Manus et al. ............... 600/484 |
| 4,757,815 A | * | 7/1988 | Strandberg et al. ........... 607/20 |
| 4,930,517 A | | 6/1990 | Cohen et al. |
| 4,930,518 A | * | 6/1990 | Hrushesky ................. 600/484 |
| 5,466,245 A | * | 11/1995 | Spinelli et al. .............. 607/17 |
| 5,584,868 A | | 12/1996 | Salo et al. |
| 5,749,900 A | * | 5/1998 | Schroeppel et al. ........... 607/4 |
| 5,843,138 A | * | 12/1998 | Evers et al. .................. 607/30 |
| 6,047,211 A | | 4/2000 | Swanson et al. |
| 6,141,590 A | * | 10/2000 | Renirie et al. ................ 607/20 |
| 6,275,727 B1 | | 8/2001 | Hopper et al. |
| 6,415,183 B1 | | 7/2002 | Scheiner et al. |
| 6,454,719 B1 | * | 9/2002 | Greenhut .................... 600/484 |
| 6,456,256 B1 | | 9/2002 | Amundson et al. |
| 6,459,929 B1 | * | 10/2002 | Hopper et al. .............. 600/513 |
| 6,589,188 B1 | * | 7/2003 | Street et al. ................. 600/538 |
| 6,594,511 B2 | * | 7/2003 | Stone et al. ................. 600/324 |
| 6,751,499 B2 | * | 6/2004 | Lange et al. ................. 600/544 |
| 6,858,006 B2 | * | 2/2005 | MacCarter et al. ......... 600/300 |
| 6,882,883 B2 | * | 4/2005 | Condie et al. ................ 607/11 |
| 6,942,622 B1 | * | 9/2005 | Turcott ....................... 600/508 |
| 2002/0151812 A1 | | 10/2002 | Scheiner et al. |
| 2002/0161412 A1 | | 10/2002 | Sun et al. |

OTHER PUBLICATIONS

Steven Lehrer, M.D., Understanding Lung Sounds, Second Ed., Copyright 1993, 1984 by W.B. Saunders Company pp. 91-105.
J.P. Saul, R.J. Cohen, Respiratory Sinus Arrhythmia, Vagal Control of the Heart: Experimental Basis and Clinical Implications edited by M.N. Levy, P.J. Schwartz, copyright 1994, Futura Publishing Co., In., Armonk, NY, pp. 511-537.
M.R. Cowie, D.A. Wood, A.J.S. Coats, S.G. Thompson, V. Suresh, P.A. Poole-Wilson, G.C. Sutton, Survival of Patients with a New Diagnosis of Heart Failure: A Population Based Study, Heart 2000; 83:505-510.

* cited by examiner

*Primary Examiner*—Carl Layno
*Assistant Examiner*—Brian T. Gedeon
(74) *Attorney, Agent, or Firm*—Hollingsworth & Funk, LLC (57) ABSTRACT

An apparatus for measuring a patient's heart rate response to respiration, for monitoring the patient's autonomic tone, includes an implantable system. The implantable system includes a sensor for generating sensed signals representing detected beat-to-beat heart rate. Further, the implantable system includes a sensor for generating sensed signals representing detected respiration. The implantable system also includes an element for estimating the sensitivity of heart rate to respiration, responsive to the sensed heart rate and respiration signals.

56 Claims, 4 Drawing Sheets

MEASUREMENT OF RESPIRATORY SINUS ARRHYTHMIA USING RESPIRATORY AND ELECTROGRAM SENSORS IN AN IMPLANTABLE DEVICE

BACKGROUND OF THE INVENTION

1. Field of the Invention

The invention relates generally to systems and methods for use in the treatment of congestive heart failure, and, more particularly, to systems and methods for measuring a patient's heart rate response to respiration for monitoring the patient's autonomic function.

2. Description of the Related Art

Cardiac pacemakers generally provide functions including sensing electrical signals generated by the heart, controlling stimulation of excitable tissues in the heart, sensing the response of the heart to such stimulation, and responding to inadequate or inappropriate stimulus or response, e.g., dysrhythmia, to deliver therapeutic stimuli to the heart. Some existing cardiac pacemakers also function to communicate with an external programmer device to support a variety of monitoring, diagnostic and configuration functions.

Certain cardiac pacemakers include internal sensors which can provide information valuable for this purpose, such as a transthoracic impedance sensor. This sensor can be used to monitor the patient's respiration. If the person's minute ventilation becomes high enough, it is an indication that their heart rate needs to be increased to meet metabolic demand.

Cardiac Resynchronization Therapy (CRT) is a relatively new but promising therapy for the treatment of congestive heart failure (CHF). CRT is a method of applying cardiac pacing therapy in a failing heart, that establishes more normal ventricular wall and atrial-ventricular synchrony. In CRT, a pacemaker may be implanted to restore synchrony to the beating of the heart, thereby increasing the heart's pumping efficiency.

CHF patients represent a large and growing population of patients that can benefit from implantable devices. CHF as a disease comprises a complicated set of interrelated systemic dysfunctions, involving the cardiac and circulatory systems, the autonomic system, renal system, and the respiratory system.

Due to the complex nature of CHF, in order to understand and track the progression of the disease, it is necessary to monitor a variety of symptoms presented by the affected systems. An implanted device is in a unique position to aid the CHF physician because of its ability to monitor a number of the symptoms of CHF over extended periods of time. In particular, many implanted devices are able to monitor heart beat intervals on a beat-by-beat basis, and some implanted devices also are able to monitor respiratory patterns of the patients.

Respiratory Sinus Arrhythmia (RSA), a phenomenon that has been known to physicians for centuries, describes the change of heart rate with respiration. Generally, in healthy persons, resting heart rate increases simultaneously with inspiration, with the magnitude of the effect being directly related to the depth of respiration, and also somewhat affected by the respiration rate. The phase of the response is also somewhat affected by the respiration rate. In general, RSA decreases with age, and diseases such as CHF can lead to greatly diminished RSA. Studies have shown RSA to be mediated predominantly but not entirely by vagal control of the heart.

A large portion of a healthy person's heart rate variability (HRV) is due to RSA. In fact, the high frequency (HF) component is almost entirely due to RSA. Since RSA contributes significantly to overall HRV, and in fact dominates the HF portion of HRV, and since RSA is generally proportional to the depth of respiration, it follows that the depth of respiration will to some degree affect many measures of HRV, particularly those specifically dependent on the HF part of the HRV spectrum. Abnormal respiration patterns may affect all components of HRV.

RSA is potentially a more accurate measure of vagal tone than HRV which analyzes heart beat intervals without any attempt to quantify or distinguish between the many factors that may be responsible for heart rate (HR) fluctuations. Measures of autonomic function based on HRV alone may be limited in accuracy and specificity because they can be affected by variable and/or abnormal respiration patterns. In particular, shallow breathing due to congestion may itself lead to a reduced high-frequency HRV component unrelated to the autonomic tone of the patient. RSA is a ratio which is a specific measure of the response of HR to a given input (respiration). Further specificity may be provided by monitoring and correcting for activity, posture, and other variables.

Hence, those skilled in the art have recognized a need for providing a system which is capable of monitoring a patient's autonomic function, by RSA measurement of the patient's heart rate response to respiration. The invention fulfills these needs and others.

SUMMARY OF THE INVENTION

Briefly, and in general terms, the invention is directed to implantable devices which have a number of diagnostic features for monitoring patient status. CRT provides therapy for the treatment of a chronic disease, CHF, whereby patient diagnostics have become a more important part of what can be provided continuously with an implanted device.

The present invention is directed to detecting and monitoring signs of CHF in a patient. To compute a measure of RSA for detecting and monitoring CHF, the invention is able to simultaneously sense respiration and heart rate (HR). A pulse generator (PG) with an impedance-based respiration sensor includes the necessary sensing means. The respiratory waveforms provided by a transthoracic impedance sensor can be used in conjunction with an intra-cardiac electrogram sensor to monitor the heart rate change related to respiration. This represents the vagal control of the heart rate at those frequencies, since nearly all the heart rate variability at respiratory frequencies is due to respiration controlling the sinus node through vagal innervation. Changes in autonomic function often associated with heart failure result in withdrawal of vagal tone, which will result in a reduction of the RSA, so that monitoring the RSA may provide an objective measure of the severity of the patient's CHF condition.

In one aspect, the invention relates to providing a system for measuring RSA, to monitor a patient's autonomic function, for more accurate monitoring of autonomic function independent of varying respiration patterns associated with CHF, to provide an objective measure of the severity of the patient's HF condition.

In a detailed aspect, the system is able to simultaneously sense the patient's respiration and beat-to-beat heart rate, for measuring parasympathetic vagal responsiveness. It includes an electrogram sensor, for sensing the patient's beat-to-beat heart rate for generating a heart rate signal.

Further, the system includes a respiration sensor, for sensing the patient's respiration and generating a respiration signal. The system also provides a heart rate-respiration sensitivity estimating element, for estimating the sensitivity of heart rate to respiration, responsive to the generated heart rate signal and the generated respiration signal.

These and other aspects and advantages of the invention will become apparent from the following detailed description and the accompanying drawings which illustrate by way of example the features of the invention.

DETAILED DESCRIPTION OF THE PREFERRED EMBODIMENTS

Figure 1:
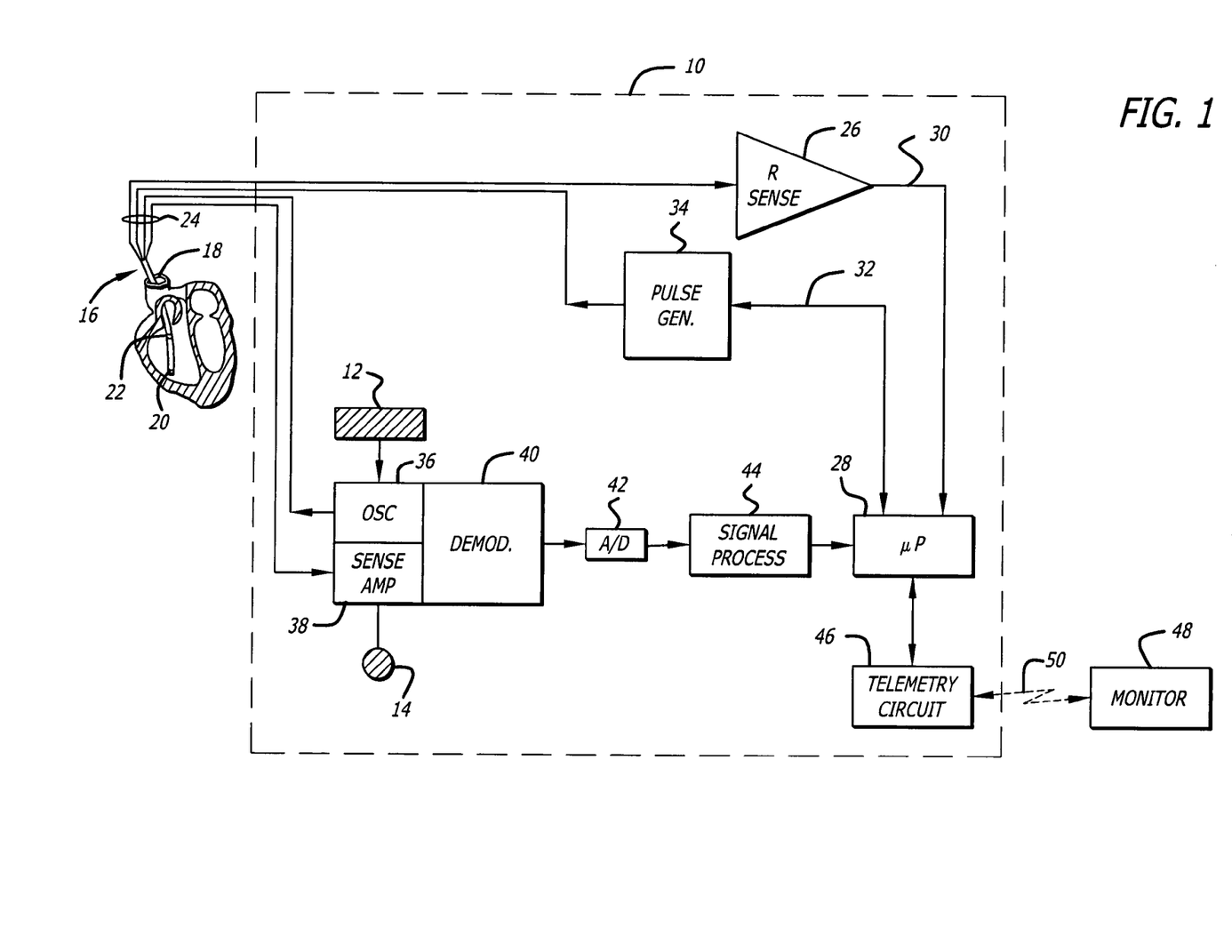
FIG. 1 is a block diagram representation of an implantable system in accordance with the present invention.
Figure 2:
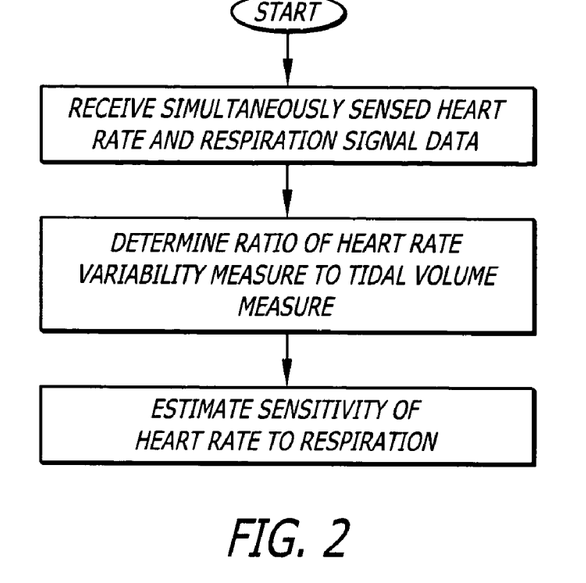
FIGS. 2-7 are flow charts illustrating methods of estimating sensitivity of heart rate to respiration in accordance with the present invention.
Figure 3:
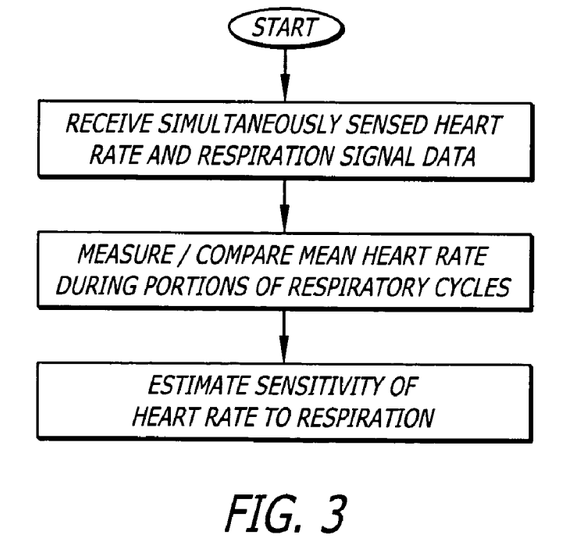
Figure 4:
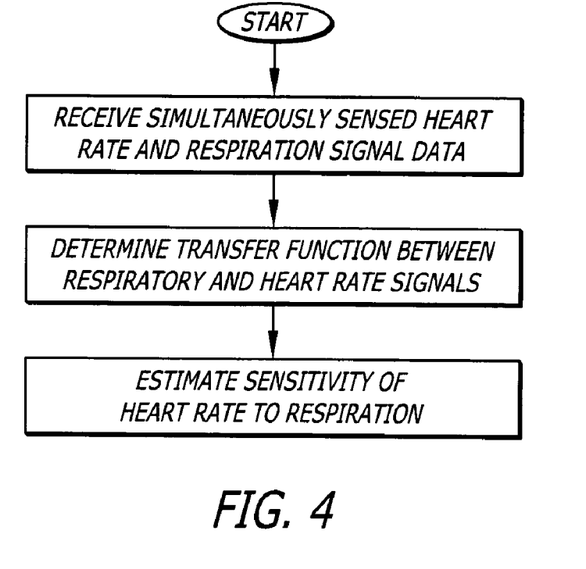
Figure 5:
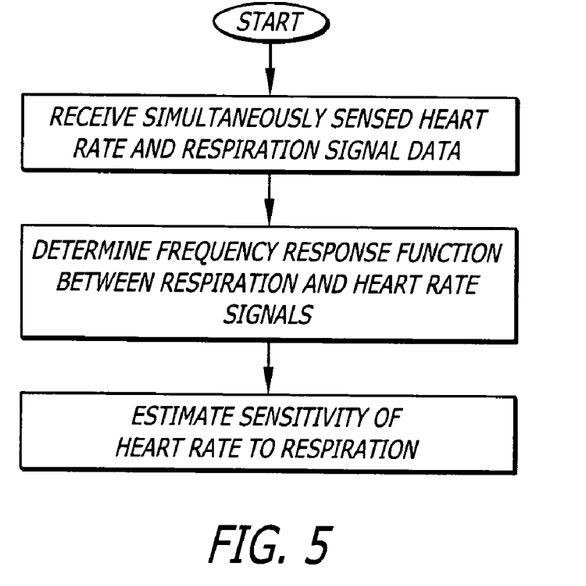
Figure 6:
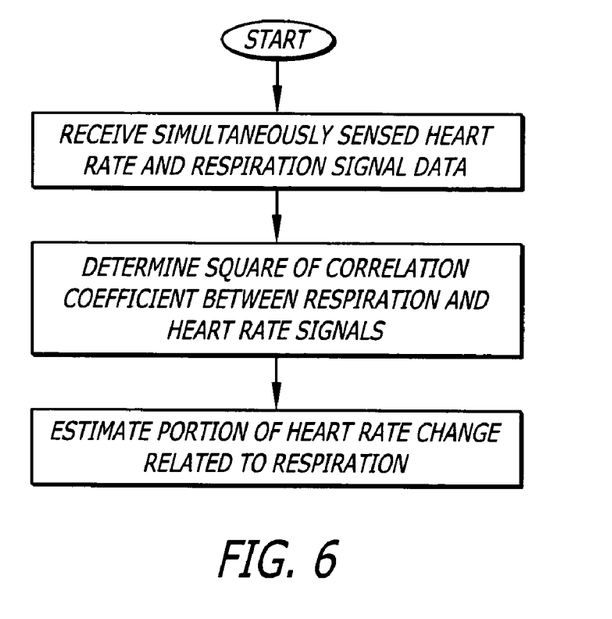
Figure 7:
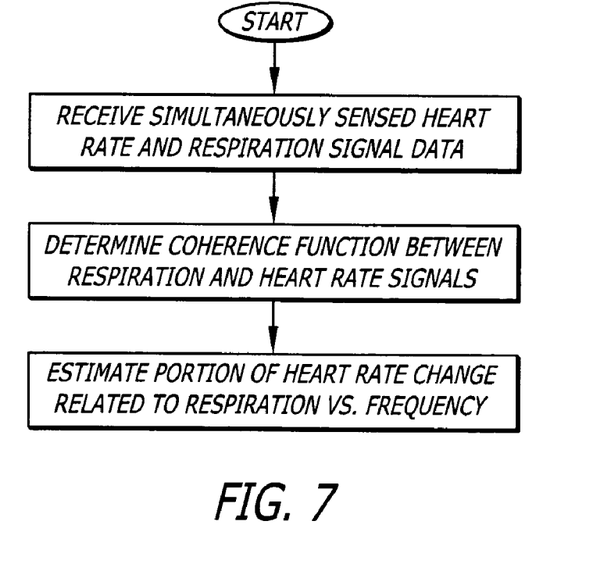

Referring now to the drawings, wherein the reference numerals denote like or corresponding parts throughout the figures, and particularly to FIG. 1, there is shown a system for measuring respiratory sinus arrhythmia, to monitor a patient's autonomic function.

The present invention is concerned with implantable, long-term monitoring of RSA. It uses simultaneously-operating intracardiac electrogram heart interval and transthoracic impedance respiration sensors. It does not need to fully specify the transfer function at all frequencies, and can use natural variations in respiration signal over a long time period (i.e. a full day) rather than requiring broadband perturbations in respiration. In particular, the system utilizes the breathing which the patient is undergoing, and computes the RSA at the frequencies at which the patient naturally breathes, instead of having the patient breathe at randomly spaced intervals to fully specify the whole frequency transfer function spectrum of the patient's breathing as an input to the system.

To the degree that RSA can be approximated as a linear, time-invariant system, one can characterize it by determining the transfer function of a system with a respiration signal as its input and a heart rate signal as the output. Thus, if one has a platform with simultaneous sensing of the respiration and beat-to-beat heart rate, one can estimate a number of quantities that characterize the sensitivity of heart rate to respiration. This sensitivity is a measure of the responsiveness of the heart to autonomic influences. In the HF region (above 0.15 Hz, where respiration typically occurs), it is a measure specifically of parasympathetic (vagal) responsiveness.

The system relates to the use of simultaneously sensed respiration and beat-to-beat heart rate signals to estimate the sensitivity of heart rate to respiration, and the use of these measures as indices of autonomic, primarily vagal, responsiveness.

The correlation between respiration and HR may be determined by computing the correlation coefficient between respiration and the HF component of HR signals, to determine the amount of HRV that is derived from respiration, or by computing the coherence function between respiration and HR signals within the HF band to determine the amount of HRV that is derived from respiration as a function of frequency.

In particular, for example, RSA may be computed by taking the ratio of the energy under the HF peak of HRV to a measure of average tidal volume, or by comparing HR during inhalation to HR at exhalation, for example by synchronous averaging of heart rate with respect to timing within the respiratory cycle, then taking the ratio of the change in HR to tidal volume. It may also be determined by computing the frequency response function (FRF) between the respiratory signal and the HR signal (magnitude vs. frequency) or by computing the transfer function (TF) between the respiratory signal and the HR signal (magnitude and phase vs. frequency).

Referring to FIG. 1, an exemplary apparatus for use in the measuring of RSA to monitor a patient's autonomic tone comprises an implantable system 10. The implantable system 10 is generally described in the context of an implantable cardiac rhythm management device configured to monitor CHF patients, for illustrative purposes only.

The implantable system 10 has a housing, shown enclosed by a broken line box, having electrodes 12 and 14 disposed thereon. Electrode 12 may comprise an uninsulated portion of a metal, typically titanium, hermetically sealed housing, while electrode 14 may be disposed on the device's header. The implantable system 10 is able to be coupled to a patient's heart by an electrical lead assembly 16 comprising a body member 18 having a distal tip electrode 20 and a ring electrode 22 affixed to the surface thereof. Body member 18 is typically flexible, elongated, and tubular, and is comprised of a biocompatible material. Extending the length of the lead are electrical conductors 24 that connect through electrical contacts in the lead barrel to the internal circuitry of the implantable system 10.

The cardiac rhythm management device in the implantable system 10, which is contained within the hermetically sealed housing, includes an R-wave sensing amplifier 26 that picks up and amplifies ventricular depolarization signals picked up by the electrode 20. The output from the sense amplifier 26 is applied as an input to a processor circuit 28 such as a microprocessor by way of conductor 30. The microprocessor 28, following a stored program, provides a control signal on line 32 to a pulse generator 34 whose output signal is applied over one of the conductors 24 to the tip electrode 20 for stimulating and thereby evoking a paced response from the heart.

The implantable system 10 includes an electrogram sensor, for sensing the patient's beat-to-beat heart rate and generating a heart rate signal. The electrogram sensor comprises an intracardiac electrogram heart interval sensor. The intracardiac electrogram heart interval sensor measures the electricity of the heart through an electrode in the heart, to obtain a localized view of the electrical activity of the heart for measuring heart rate. It senses the voltage output of the heart, and may be implemented with bipolar leads comprised of a pair of closely spaced electrodes.

The electrogram sensor measures the voltage between the electrodes as indicative of the electrical discharge of the heart, generating an electrogram signal. In particular, circuitry and/or signal processing means is provided for sensing beat-to-beat heart rate from the electrogram signal, constituting an intracardiac electrogram heart rate sensor. The implantable system 10 further includes a respiration sensor, for sensing the patient's respiration and generating a respiration signal. The respiration sensor comprises a transthoracic impedance respiration sensor. In this regard, there is provided an oscillator 36 which, when activated, produces an alternating current of a predetermined frequency, typically in a range of from about 2000 Hz to 5000 Hz and of an amplitude below about ten microamperes, which ensures that the output from the oscillator will not stimulate heart tissue. This signal is preferably applied between the electrode 12 on the implantable system 10 and the ring electrode 22 on the lead, and comprises an AC carrier signal that is modulated by the influx and outflow of blood from the right ventricle and by inflation and deflation of the intervening lung tissue. A voltage signal due to the modulated carrier signal is developed between the tip electrode 20 and the electrode 14 on the device's header and is amplified by sense amplifier 38, and then demodulated by demodulator circuit 40, to remove the modulating envelope from the carrier. The envelope signal is a measure of instantaneous impedance as a function of time. The impedance vs. time (Z vs. t) analog signal is converted to a digital format by A/D converter 42 for digital signal processing, and is then applied to a signal processing circuit 44 for signal processing to derive heart related factors.

The electrode 12 is disposed on the housing of the implantable system 10. Upon implanting the implantable system 10, the electrode 12 is located subcutaneously proximate the pectoral muscles of the chest, while the electrode 22 is disposed with the heart, resulting in modulation which has a major component attributable to respiratory activity. The raw signal is a combination of respiratory and heart related activity, which are filtered out on the basis of their frequency. Since the heart is generally beating faster than the breathing, the higher frequency signal is filtered out to get the signal indicative of respiration itself. The respiration signal derived from the transthoracic impedance waveform can be signal processed to derive respiratory related factors including respiratory rate, tidal volume, inspiratory time, expiratory time, and minute ventilation.

The electrogram sensor and the respiration sensor are able to simultaneously sense the patient's beat-to-beat heart rate and respiration. Also, the implantable system 10 includes a heart rate-respiration sensitivity estimating element, for estimating the sensitivity of heart rate to respiration, responsive to the sensed heart rate from the electrogram sensor and the sensed respiration from the respiration sensor. The heart rate-respiration sensitivity estimating element comprises a processor which processes responsive to a stored program. The digitally processed signals from the respiration sensor and the electrogram sensor are processed in the microprocessor 28. Some or all of the processing may be performed by an off-board external processing system, to provide increased processing power and flexibility.

As shown in FIGS. 2-7, the processor is able to determine an estimation of heart rate-respiration sensitivity for RSA measuring, responsive to the sensor signals. For example, the processor is able to estimate the sensitivity by determining the ratio of a measure of heart rate variability to a measure of tidal volume. The measure of heart rate variability may comprise the energy of the high frequency peak thereof. Tidal volume measurement would be the peak to valley readings of the transthoracic impedance sensor. Further, the processor is able to estimate the sensitivity by measuring the mean heart rate during one portion of the respiratory cycle and comparing the mean heart rate at another portion of the respiratory cycle. It may comprise determining the ratio of the change in heart rate to the tidal volume. The one portion of the respiratory cycle may comprise exhalation, and the other portion may comprise inhalation. The processor is also able to estimate the sensitivity by determining the frequency response function between the respiration signal and the heart rate signal. The frequency response function represents the sensitivity of heart rate to respiration as a function of frequency. The measuring and comparing may comprise synchronous averaging. The processor is still further able to estimate the sensitivity by determining the transfer function between the respiration signal and the heart rate signal. The transfer function represents the sensitivity and time delay of the heart rate response to respiration as a function of frequency.

The processor is also able to estimate the square of the correlation coefficient between the respiration signal and the heart rate signal or the HF portion thereof, for determining the relative amount of heart rate variability which is derived from respiration. The correlation coefficient is the signal processing function of quantifying the amount of the output due to a given input, and in particular is the quantifying of the amount of the output change in heart rate which is due to the input respiration signal. The processor is further able to estimate the coherence function between the respiration signal and the heart rate signal for determining the relative amount of heart rate variability from respiration as a function of frequency. The coherence function constitutes the frequency specific correlation coefficient. Specifically, at various points in the frequency the correlation coefficient is computed based on only that frequency. It aids in quantifying the amount of output at a particular frequency which is due to an input at that frequency. Techniques for computing the functions enumerated above and similar related functions are well known to those versed in the art of signal processing.

The implantable system 10 collects the processing results, as illustrated in FIG. 1. Trends of the processing results may be collected, for example, for weeks or for months. When the patient goes into the office, the physician may query the implantable system 10 with a wand or via a radio frequency (RF) telemetry circuit 46, which allows information stored in the microprocessor's RAM memory banks to be read out transcutaneously. The implantable system 10 may then transfer the data to a terminal, which may be an enlarged laptop computer with a flip-up liquid crystal diode screen, or to an external monitor 48 for viewing by a medical professional.

In accordance with the present invention, an implantable system is provided which, when implanted in a patient, provides for the read-out of estimates of RSA, and whereby a physician or other caregiver can monitor one or more RSA-related values or trends indicative of CHF patient status.

It can be seen that by computing and data logging RSA-related parameters within an implantable system 10 for subsequent readout and processing, valuable information on CHF patient condition can be stored over a prolonged period of time and then telemetered to a healthcare professional. One or more of the RSA-related values can be compared to corresponding values previously computed and stored to determine whether a change in therapy has proven beneficial or has resulted in a worsening of the patient's CHF status. If so, a programmable parameter of the CRM can be adjusted accordingly in either a closed-loop (automatic) or open-loop (manual) fashion.

The system output may constitute for example a series of daily trend points quantifying the patient's RSA for that day, measured automatically and possibly throughout the day. Such output may alternatively include months worth of daily measurement points, whereby when the patient comes in to the physician's office for a follow-up appointment, every three months for example, then the implanted device has stored months worth of daily time trend points, so the physician can see changes over time. The system output may be monitored through radio frequency communication, as for example by a bedside monitor, which may be part of the system whereby, when the patient lies down at home to go to bed, a daily transfer would occur, which would be transparent to the patient, and would require no action on the patient's part. The information may be transferred through the Internet to a central server, whereby displays could then be available for the doctor and/or the patient. Alerts could be issued to the doctor if alarming conditions are noted.

This invention has been described to provide those skilled in the art with the information needed to make and use the invention. However, it is to be understood that the invention can be carried out by specifically different equipment, devices, and mathematical functions, and that various modifications, both as to the equipment, operating procedures, and mathematical functions, can be accomplished without departing from the scope of the invention itself.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A system for measuring respiratory sinus arrhythmia, to monitor a patient's autonomic function, comprising:
    a heart beat interval sensor, for sensing the patient's beat-to-beat heart rate and generating a heart rate signal;
    a respiration sensor, for sensing the patient's respiration and generating a respiration signal; and
    a heart rate-respiration sensitivity estimating element, for estimating the sensitivity of heart rate to respiration as measurements of respiratory sinus arrhythmia, responsive to the heart rate signal from the heart beat interval sensor and the respiration signal from the respiration sensor, and using the sensitivity estimation as an indicia of autonomic responsiveness in autonomic function monitoring.

2. The system of claim 1, wherein the heart beat interval sensor and the respiration sensor are adapted to simultaneously sense the patient's beat-to-beat heart rate and respiration.

3. The system of claim 1, wherein the heart beat interval sensor and the respiration sensor are associated with an implantable device.

4. The system of claim 1, wherein the heart rate-respiration sensitivity estimating element is further adapted to generate trends in the measurements of respiratory sinus arrhythmia.

5. The system of claim 1, further comprising a measurements monitoring element for enabling the monitoring of the measurements of respiratory sinus arrhythmia.

6. The system of claim 1, further adapted to enable the measurements of respiratory sinus arrhythmia to be compared for enabling a determination regarding whether to adjust a therapy for a patient.

7. The system of claim 1, wherein the heart rate-respiration sensitivity estimating element is adapted to estimate the sensitivity by determining the ratio of a measure of heart rate variability to a measure of tidal volume.

8. The system of claim 1, wherein the heart rate-respiration sensitivity estimating element is adapted to estimate the sensitivity by measuring the mean heart rate during one portion of the respiratory cycle and measuring the mean heart rate at another portion of the respiratory cycle.

9. The system of claim 1, wherein the heart rate-respiration sensitivity estimating element is adapted to estimate the sensitivity by determining the transfer function between the respiration signal and the heart rate signal.

10. The system of claim 1, wherein the heart rate-respiration sensitivity estimating element is adapted to estimate the sensitivity by determining the frequency response function between the respiration signal and the heart rate signal.

11. The system of claim 1, wherein the heart beat interval sensor comprises an intracardiac electrogram heart beat interval sensor.

12. The system of claim 1, wherein the respiration sensor comprises a trans-thoracic impedance respiration sensor.

13. The system of claim 1, wherein the heart rate-respiration sensitivity estimating element comprises a processor.

14. The system of claim 2, wherein the implantable device comprises a pulse generator, and the electrogram sensor and the respiration sensor are associated with the pulse generator.

15. The system of claim 4, wherein the heart rate-respiration sensitivity estimating element is further adapted to collect the generated trends in the measurements of respiratory sinus arrhythmia.

16. The system of claim 5, wherein the measurements monitoring element is further adapted to enable the monitoring of the trends of the measurements of respiratory sinus arrhythmia.

17. The system of claim 6, further adapted to enable the trends of the measurements of respiratory sinus arrhythmia to be compared for enabling a determination regarding whether to adjust a therapy for a patient.

18. The system of claim 7, wherein the measure of heart rate variability comprises a measure of the strength of the high frequency peak thereof.

19. The system of claim 7, wherein the measure of tidal volume comprises the peak to valley readings of the respiration sensor.

20. The system of claim 8, further comprising determining the ratio of the change in heart rate to the tidal volume.

21. The system of claim 8, wherein the one portion of the respiratory cycle comprises exhalation, and the other portion of the respiratory cycle comprises inhalation.

22. The system of claim 8, wherein the measuring and comparing comprises synchronous averaging.

23. The system of claim 13, wherein the heart rate-respiration sensitivity estimating element is adapted to compute measurements of respiratory sinus arrhythmia.

24. The system of claim 13, wherein the heart rate-respiration sensitivity estimating element further comprises an implantable processor.

25. The system of claim 13, wherein the heart rate-respiration sensitivity estimating element further comprises a patient-external processor.

26. The system of claim 23, wherein the processor is further adapted to data log the computed measurements of respiratory sinus arrhythmia.

27. A system for measuring respiratory sinus arrhythmia, to monitor a patient's autonomic function, comprising:
    a heart beat interval sensor, for sensing the patient's beat-to-beat heart rate and generating a heart rate signal;
    a respiration sensor, for sensing the patient's respiration and generating a respiration signal; and
    heart rate-respiration sensitivity estimating means for estimating the sensitivity of heart rate to respiration, responsive to the heart rate signal from the heart beat interval sensor and the respiration signal from the respiration sensor, and using the sensitivity estimation as an indicia of autonomic responsiveness in autonomic function monitoring.

28. A system for measuring respiratory sinus arrhythmia, to monitor a patient's autonomic function, comprising:
   a heart beat interval sensor, for sensing the patient's beat-to-beat heart rate and generating a heart rate signal;
   a respiration sensor, for sensing the patient's respiration and generating a respiration signal; and
   a heart rate-respiration measuring element, for measuring the relative amount of heart rate variability due to respiration, responsive to the heart rate signal from the heart beat interval sensor and the respiration signal from the respiration sensor, and using the measured relative amount of heart rate variability due to respiration as an indicia of autonomic responsiveness in autonomic function monitoring.

29. The system of claim 28, wherein the heart rate-respiration sensitivity estimating element is adapted to determine the square of the correlation coefficient between the respiration signal and the heart rate signal for determining the relative amount of heart rate variability which is derived from respiration.

30. The system of claim 28, wherein the heart rate-respiration sensitivity estimating element is adapted to estimate the coherence function between the respiration signal and the heart rate signal for determining the relative amount of heart rate variability from respiration as a function of frequency.

31. A method of measuring respiratory sinus arrhythmia, to monitor a patient's autonomic function, in a system which comprises a heart beat interval sensor, for sensing the patient's beat-to-beat heart rate and generating a heart rate signal, a respiration sensor, for sensing the patient's respiration and generating a respiration signal, and a heart rate-respiration sensitivity estimating element, for estimating the sensitivity of heart rate to respiration as measurements of respiratory sinus arrhythmia, responsive to the heart rate signal from the heart beat interval sensor and the respiration signal from the respiration sensor, wherein the method comprises:
   heart rate sensing of the patient's beat-to-beat heart rate and the generating of a heart rate signal, by the heart beat interval sensor;
   respiration sensing of the patient's respiration and the generating of a respiration signal, by the respiration sensor;
   estimating the sensitivity of heart rate to respiration, responsive to the heart rate signal from the heart beat interval sensor and the respiration signal from the respiration sensor, by the heart rate-respiration sensitivity estimating element; and
   tracking the sensitivity estimation as an indicia of autonomic responsiveness in autonomic function monitoring.

32. The method of claim 31, wherein the heart beat interval sensor and the respiration sensor are adapted to simultaneously sense the patient's beat-to-beat heart rate and respiration, and wherein heart rate sensing and respiration sensing further comprise simultaneously sensing the patient's beat-to-beat heart rate and respiration.

33. The method of claim 31, wherein the heart beat interval sensor and the respiration sensor are associated with an implantable device, and wherein heart rate sensing and respiration sensing are associated with an implantable device.

34. The method of claim 31, wherein the heart rate-respiration sensitivity estimating element is further adapted to generate trends in the measurements of respiratory sinus arrhythmia, and wherein estimating further comprises generating trends in the measurements of respiratory sinus arrhythmia.

35. The method of claim 31, further comprising a measurements monitoring element for enabling the monitoring of the measurements of respiratory sinus arrhythmia, and further comprising monitoring the measurements of respiratory sinus arrhythmia by the measurements monitoring element.

36. The method of claim 31, further adapted to enable the measurements of respiratory sinus arrhythmia to be compared for enabling a determination regarding whether to adjust a therapy for a patient, further comprising comparing the measurements of respiratory sinus arrhythmia for enabling the determination regarding whether to adjust the patient's therapy.

37. The method of claim 31, wherein the heart rate-respiration sensitivity estimating element is adapted to estimate the sensitivity by determining the ratio of a measure of heart rate variability to a measure of tidal volume, and wherein estimating comprises determining the ratio of the measure of heart rate variability to the measure of tidal volume.

38. The method of claim 31, wherein the heart rate-respiration sensitivity estimating element is adapted to estimate the sensitivity by measuring the mean heart rate during one portion of the respiratory cycle and measuring the mean heart rate at another portion of the respiratory cycle, and wherein estimating comprises comparing the mean heart rate during the one portion of the respiratory cycle to the mean heart rate at the other portion of the respiratory cycle.

39. The method of claim 31, wherein the heart rate-respiration sensitivity estimating element is adapted to estimate the sensitivity by determining the transfer function between the respiration signal and the heart rate signal, and wherein estimating comprises determining the transfer function between the respiration signal and the heart rate signal.

40. The method of claim 31, wherein the heart rate-respiration sensitivity estimating element is adapted to estimate the sensitivity by determining the frequency response function between the respiration signal and the heart rate signal, and wherein estimating comprises determining the frequency response function between the respiration signal and the heart rate signal.

41. The method of claim 31, wherein the heart beat interval sensor comprises an intracardiac electrogram heart beat interval sensor, and wherein heart rate sensing further comprises heart rate sensing by the intracardiac electrogram heart beat interval sensor.

42. The method of claim 31, wherein the respiration sensor comprises a trans-thoracic impedance respiration sensor, and wherein respiration sensing comprises respiration sensing by the trans-thoracic impedance respiration sensor.

43. The method of claim 31, wherein the heart rate-respiration sensitivity estimating element comprises a processor, and wherein estimating comprises estimating by the processor.

44. The method of claim 32, wherein the implantable device comprises a pulse generator, and the electrogram sensor and the respiration sensor are associated with the pulse generator, and wherein heart rate sensing and respiration sensing are associated with the pulse generator.

45. The method of claim 35, wherein the heart rate-respiration sensitivity estimating element is further adapted to collect the generated trends in the measurements of respiratory sinus arrhythmia, and wherein estimating further comprises collecting the generated trends in the measurements of respiratory sinus arrhythmia.

46. The method of claim 37, wherein the measure of heart rate variability comprises a measure of the strength of the high frequency peak thereof, and wherein determining comprises determining the ratio of the measure of the strength of the high frequency peak of heart rate variability to the measure of tidal volume.

47. The method of claim 37, wherein the measure of tidal volume comprises the peak to valley readings of the respiration sensor, and wherein determining comprises determining the ratio of the measure of heart rate variability to the peak to valley readings of the respiration sensor.

48. The method of claim 38, further comprising determining the ratio of the change in heart rate to the tidal volume.

49. The method of claim 38, wherein the one portion of the respiratory cycle comprises exhalation, and the other portion of the respiratory cycle comprises inhalation, and wherein determining comprises measuring the mean heart rate during exhalation and comparing the mean heart rate during inhalation.

50. The method of claim 38, wherein the measuring and comparing comprises synchronous averaging.

51. The method of claim 43, wherein the heart rate-respiration sensitivity estimating element further comprises an implantable processor, and wherein estimating comprises estimating by the implantable processor.

52. The method of claim 41, wherein the heart rate-respiration sensitivity estimating element further comprises a patient-external processor, and wherein estimating further comprises estimating by the patient-external processor.

53. A method of measuring respiratory sinus arrhythmia, to monitor a patient's autonomic function, in a system which comprises a heart beat interval sensor, for sensing the patient's beat-to-beat heart rate and generating a heart rate signal, a respiration sensor, for sensing the patient's respiration and generating a respiration signal, and heart rate-respiration sensitivity estimating means, for estimating the sensitivity of heart rate to respiration as measurements of respiratory sinus arrhythmia, responsive to the heart rate signal from the heart beat interval sensor and the respiration signal from the respiration sensor, wherein the method comprises:
  heart rate sensing of the patient's beat-to-beat heart rate and the generating of a heart rate signal, by the heart beat interval sensor;
  respiration sensing of the patient's respiration and the generating of a respiration signal, by the respiration sensor; and
  estimating the sensitivity of heart rate to respiration as measurements of respiratory sinus arrhythmia, responsive to the heart rate signal from the heart beat interval sensor and the respiration signal from the respiration sensor, and using the sensitivity estimation as an indicia of autonomic responsiveness in autonomic function monitoring, by the heart rate-respiration sensitivity estimating means.

54. A method of measuring respiratory sinus arrhythmia, to monitor a patient's autonomic function, in a system which comprises a heart beat interval sensor, for sensing the patient's beat-to-beat heart rate and generating a heart rate signal, a respiration sensor, for sensing the patient's respiration and generating a respiration signal, and a heart rate-respiration measuring element, for measuring of the relative amount of heart rate variability due to respiration, responsive to the heart rate signal from the heart beat interval sensor and the respiration signal from the respiration sensor, wherein the method comprises:
  heart rate sensing of the patient's beat-to-beat heart rate and the generating of a heart rate signal, by the heart beat interval sensor;
  respiration sensing of the patient's respiration and the generating of a respiration signal, by the respiration sensor; and
  measuring the relative amount of heart rate variability due to respiration, responsive to the heart rate signal from the heart beat interval sensor and the respiration signal from the respiration sensor, and using the measured relative amount of heart rate variability due to respiration as an indicia of autonomic responsiveness in autonomic function monitoring, by the heart rate-respiration comparing element.

55. The method of claim 54, wherein the heart rate-respiration sensitivity estimating element is adapted to determine the square of the correlation coefficient between the respiration signal and the heart rate signal for determining the relative amount of heart rate variability which is derived from respiration, and wherein estimating comprises determining the square of the correlation coefficient between the respiration signal and the heart rate signal for determining the relative amount of heart rate variability which is derived from respiration.

56. The method of claim 54, wherein the heart rate-respiration sensitivity estimating element is adapted to estimate the sensitivity by determining the coherence function between the respiration signal and the heart rate signal for determining the relative amount of heart rate variability from respiration as a function of frequency, and wherein estimating comprises determining the coherence function between the respiration signal and the heart rate signal for determining the relative amount of heart rate variability from respiration as a function of frequency.

* * * * *